US007853317B2

(12) United States Patent
Duann et al.

(10) Patent No.: US 7,853,317 B2
(45) Date of Patent: Dec. 14, 2010

(54) METHOD AND SYSTEM FOR CARDIAC SIGNAL DECOMPOSITION

(75) Inventors: Jeng-Ren Duann, San Diego, CA (US); Tzyy-Ping Jung, San Diego, CA (US)

(73) Assignee: Sigmed, Inc., San Diego, CA (US)

( * ) Notice: Subject to any disclaimer, the term of this patent is extended or adjusted under 35 U.S.C. 154(b) by 274 days.

(21) Appl. No.: 11/577,227

(22) PCT Filed: Oct. 13, 2005

(86) PCT No.: PCT/US2005/037082
§ 371 (c)(1),
(2), (4) Date: Apr. 13, 2007

(87) PCT Pub. No.: WO2006/044699
PCT Pub. Date: Apr. 27, 2006

(65) Prior Publication Data
US 2008/0097537 A1    Apr. 24, 2008

Related U.S. Application Data

(60) Provisional application No. 60/618,226, filed on Oct. 13, 2004.

(51) Int. Cl.
*A61B 5/04* (2006.01)
(52) U.S. Cl. .................. 600/509; 600/513; 600/517
(58) Field of Classification Search ......... 600/500–512, 600/515, 484; 607/4–9, 115–118
See application file for complete search history.

(56) References Cited

U.S. PATENT DOCUMENTS 5,215,099 A    6/1993    Haberl et al.
(Continued)

FOREIGN PATENT DOCUMENTS

EP    1190671 A2    3/2002

(Continued)

OTHER PUBLICATIONS

Barros et al., Removing artifacts from electrographic signals using independent components analysis, NEUROCOMPUTING, 1998, pp. 173-186, vol. 22. Iss. 1-3, Elsevier, London, UK.

(Continued)

*Primary Examiner*—Carl H Layno
*Assistant Examiner*—Paula J Stice
(74) *Attorney, Agent, or Firm*—Daniel M. Chambers; BioTechnology Law Group (57) ABSTRACT

A method and system decomposes a cardiac signal, such as an electrocardiogram (ECG) signal, into components. The components are then usable to assist in the detection of an abnormal heart condition. More particularly, a single lead sensor is used to generate a single lead cardiac signal. The cardiac signal is segmented into a set of cycle segments according to detected heart waveforms. The cycle segments are aligned and used to generate a set of cross-sectional signals. The cross-sectional signals are aligned and presented as inputs to a signal separation process, which separates the cardiac signal into a set of components. The components may be grouped according to predefined criteria. The components or groups may be analyzed or displayed to assist in the detection of an abnormal cardiac signal, which may be indicative of an abnormal heart condition. In one example, the signal separation process is a non-orthogonal transformation method such as independent component analysis (ICA).

18 Claims, 6 Drawing Sheets

U.S. PATENT DOCUMENTS

| | | | |
|---|---|---|---|
| 5,439,004 | A | 8/1995 | Duong-Van et al. |
| 5,706,402 | A | 1/1998 | Bell |
| 6,152,883 | A | 11/2000 | Blanchett et al. |
| 6,725,085 | B2 * | 4/2004 | Schwartzman et al. ...... 600/509 |
| 7,343,198 | B2 * | 3/2008 | Behbehani et al. ......... 600/509 |
| 2003/0208109 | A1 | 11/2003 | David et al. |
| 2004/0010201 | A1 * | 1/2004 | Korzinov et al. ............ 600/518 |
| 2004/0019287 | A1 | 1/2004 | White |
| 2004/0054295 | A1 | 3/2004 | Ramseth |
| 2004/0193064 | A1 * | 9/2004 | Shusterman ................ 600/504 |

FOREIGN PATENT DOCUMENTS

| | | |
|---|---|---|
| EP | 1773188 A1 | 4/2007 |
| WO | 0124876 A1 | 4/2001 |
| WO | 03003905 A2 | 1/2003 |

OTHER PUBLICATIONS

De Lathauwer et al., Fetal Electrocardiogram Extraction by Blind Source Subspace Separation, IEEE Transactions on Biomedical Engineering, 2000, pp. 567-572, vol. 47, No. 5, IEEE Service Center, Piscataway, NJ, US.

Jung et al., Independent Component Analysis of Biomedical Signals, Proc. 2nd Int'l Workshop on Independent Component Anal. and Blind Signal Separation, 2000, pp. 633-644, Helsinki, Finland.

Potter et al., Competing ICA techniques in biomedical signal analysis, Electrical and Computer Engineering, Canadian Conference on May 13-16, 2001, IEEE, 2001, pp. 987-992, vol. 2, IEEE Service Center, Piscataway, NJ, US.

Zarzoso et al., Noninvasive Fetal Electrocardiogram Extraction: Blind Separation Versus Adaptive Noise Cancellation, IEEE Transactions on Biomedical Engineering, 2001, pp. 12-18, vol. 48, No. 1, IEEE Service Center, Piscataway, NJ, US.

* cited by examiner

METHOD AND SYSTEM FOR CARDIAC SIGNAL DECOMPOSITION

RELATED APPLICATIONS

This application claims priority to U.S. provisional patent application No. 60/618,226, filed Oct. 13, 2004, and entitled Method and System for Cardiac Decomposition, which is incorporated herein by reference.

FIELD OF THE INVENTION

The present invention relates to the field of medical systems and methods for processing cardiac signals. More particularly, the present invention relates to the application of a signal separation process to electrocardiogram signals.

DESCRIPTION OF THE RELATED ART

An electrocardiogram (ECG/EKG) is an electrical recording of the heart and is used in the investigation of heart disease. The measurements taken are utilized in making an interpretation typically of rate/rhythm analysis and/or morphology. The measurements can be used to determine such features as the underlying rate and rhythm mechanism of the heart, the orientation of the heart (how it is placed) in the chest cavity, evidence of increased thickness (hypertrophy) of the heart muscle, evidence of damage to the various parts of the heart muscle (myocardium), evidence of acutely impaired blood flow to the heart muscle, or patterns of abnormal electric activity that may predispose the patient to abnormal cardiac rhythm disturbances. More specifically, such information can identify abnormally fast (tachycardia) slow (bradycardia) or irregular heart rhythms (arrhythmias), abnormal conduction of cardiac impulses—which may suggest underlying cardiac or metabolic disorders, occurrence of a prior heart attack (myocardial infarction), an evolving and/or acute heart attack, an acute impairment to blood flow to the heart during an episode of a threatened heart attack (unstable angina or coronary artery disease), adverse effects on the heart from various heart diseases or systemic diseases (such as high blood pressure, thyroid conditions, heart valve diseases, dilated cardiomyopathy, or other myocardial defects, etc.), adverse effects on the heart from certain lung conditions (such as emphysema, pulmonary embolus (blood clots to lung), etc.), certain congenital heart abnormalities, abnormal blood electrolytes (e.g., potassium, calcium, magnesium), inflammation of the heart or its lining (myocarditis, pericarditis).

The rhythm analysis first determines the origins of the predominant rhythm in the sample and chooses from the major categories consisting of electronic atrial pacing, atrial flutter, ectopic atrial rhythm, sinus rhythm, junction rhythm and atrial fibrillation, including asystole, tachycardia, trigeminy, bradycardia, bigeminy and atrial and ventricular fibrillations, pacemakers, implantable cardioverter defibrillator, electrical alternans—pericardial effusion, and the like. The morphology interpretation will determine the existence of ischaemic heart diseases and syndromes such as Wolff-Parkinson-White, Long QT interval Romano-Ward Syndrome and Lown-Ganong-Levine Syndrome, hypertrophy patterns such as stenosis, QRS abnormalities such as low voltage QRS, pulmonary disease pattern, QRS axis, conduction abnormalities, ventricular hypertrophy, infarction, ST+T abnormality with ventricular hypertrophy, dating infarcts, epicardial injury, pericarditis, early repolarization, nonspecific ST elevation, subendocardial injury, nonspecific ST depression, digitalis effect, junctional ST depression, ischemia, QRS-T angle and QT interval, atrioventricular (AV) block, acute pulmonary embolus, bundle branch block, hyper- and hypo-kalaemia, piggy-back heart transplant, digitalis effect, ST deviation, and other normal and abnormal signals.

Typically up to 12 leads of sensors are placed on the chest, torso, limbs, abdomen and/or back of a patient to enable the recording of multiple signals. Since each sensor generates one channel of an electronic signal, multiple sensors accommodate the recording of multiple signals. The signals are processed in the electrocardiogram device, and a display or recording is generated for use by medical personnel. The medical personnel, using their skills and training, evaluate the results to find and diagnose an abnormal cardiac signal. By using multiple channels of signals, the electrocardiogram can be used to identify or isolate abnormal heartbeats for evaluation and diagnostic purposes. However, it is time consuming and cumbersome to place multiple sensors and route their associated leads to the electrocardiogram. Further, such multi-lead packs are costly, may not be appropriately used in temporary or emergency situations, and impractical for medical personnel unless read through a long-term ECG recording for labeling abnormal heartbeats. When a 12-lead system can not be used, fewer leads may be applied, but there may be an associated decrease in the quality and detail in the resulting electrocardiogram recording. For example, a 3-lead sensor such as a Holter system may be used, typically to record the cardiac condition of a patient who is away from a hospital bed or stays at home.

Unfortunately, each channel (lead) of recorded ECG signals is typically a combination of signals from multiple sources originating from events occurring at different compartments of the heart, and strong signals such as QRS complex signals typically dominate other signals. Unwanted signals from other sources, such as signals generated by pacemakers or by non-cardiac muscle movements (such as the trembling of an elderly patient), may be included and combined in the ECG recordings. Therefore, it is desirable to separate the ECG signals into components of independent sources so that the separated components can be used for medical analysis of the patient's condition. For example, copending U.S. patent application Ser. No. 10/482,931, entitled "System and Method for Separating Cardiac Signals", discloses a system for separating a cardiac signal into its independent sources by using an independent component analysis process, and is incorporated herein by reference. Once separated, the components may be displayed or otherwise used for diagnosis and treatment.

In addition to 12-lead and 3-lead sensors, 1-lead sensors are also used, for example in ambulances or other situations when the more robust multi-lead sensors can not be used. Compared to 12-lead and 3-lead sensors, 1-lead sensors are more affordable, easier to store, and easier to use. However, such single lead sensors typically do not provide detailed cardiac information, and are therefore useful for general evaluation only. Since only limited information may be derived from the single lead system, an incorrect or incomplete evaluation and diagnosis may be made, which may result in long-term medical complications or even death. Accordingly, the single lead system is typically replaced with a multiple-lead system (preferably a 12-lead system) as soon as practical. Since only one channel of ECG signals is produced, signal processing methods that operate on multiple channels of input signals cannot be directly applied on 1-lead ECG signals. For example, an independent component analysis method requires multiple channels of input signals to separate into statistically independent components.

The standard therapy for sudden cardiac arrest is early cardioversion/defibrillation either by implantable cardioverter defibrillators (ICD) or by automatic external defibrillator (AED). An important parameter that affects the reliability and accuracy of these therapies is the algorithm or technique used to detect shockable VT and W and while avoiding unnecessary shocks possibly caused by non-shockable tachyarrhythmias (e.g. supraventricular tachycardia (SVT), atrial fibrillation (AF), etc.) and some high frequency noise commonly encountered under practical situations.

Since electrical shocks always have adverse affects on the myocardium, another primary goal of all cardiac therapies is to minimize the number and energy level of electrical signals delivered to the patient. For example, VT, which requires much lower energy levels for effective therapy, must be effectively differentiated from VF. Moreover, the safety of a device, as well as its case of use, extent of automatic operation, and widespread acceptance also depend on the performance of the arrhythmia detection system and method.

All devices and systems monitoring the cardiac state of a patient and/or generating antitachyarrhythmia therapy rely on the analysis of the electrocardiogram (ECG) from the patient. The analyses proposed and used so far were based on manipulation of information in the time-domain, frequency-domain, time-frequency domain, and bispectral domain, and even nonlinear dynamics domain. However, all these manipulations have fundamental limitations associated with the linear nature, computational complexity, or difficulty in real-time implementation as well as low sensitivity and specificity. For this reason, currently, the percentage of patients with ICDs who are paced or shocked unnecessarily exceeds 40%.

SUMMARY OF THE INVENTION

Briefly, the present invention provides a process and system to decompose a cardiac signal, such as an electrocardiogram (ECG) signal, into components. The components are then usable to assist in the detection of an abnormal heart condition. More particularly, a single lead sensor is used to generate a single lead cardiac signal. The cardiac signal is segmented into a set of cycle segments according to detected heart waveforms. The cycle segments are aligned, and a set of signals is generated, with each signal representing a cross section across the aligned cycle segments. The cross-sectional signals are then presented as inputs to a signal separation process, which separates the cardiac signal into a set of components. The components may be grouped according to predefined criteria. The components or groups may be analyzed or displayed to assist in the detection of an abnormal cardiac signal, which may be indicative of an abnormal heart condition. In one example, the signal separation process is a non-orthogonal transformation method such as independent component analysis (ICA).

In one example, the decomposition system relates to a process of decomposing a channel of ECG signals. The process includes receiving a channel of ECG signals, isolating the signals into cycles, separating the cycles of signals into statistically substantially independent components using a signal separation or decomposition process, and organizing the components into component groups. In another example, the decomposition system relates to a device for decomposing one-channel ECG signals. The device includes a signal port for receiving a single-lead cardiac signal and an associated signal receiving module. The device also has a cycle detection module for segmenting the cardiac signal into a set of cycles. The set of cycles are aligned, and a set of cross-sectional signals are generated. The cross-sectional signals are received as channel inputs to a component separation module that separates the set of cycles into statistically substantially independent components using a signal separation process. An output device, such as a display or an alarm, is active or activated responsive to detecting an abnormal cardiac signal using the independent components. The device may also include a memory for storing predefined criteria, such as frequency ranges or reference waveforms, which are indicative of an abnormality. In this way, the independent components may be selected, grouped, and compared using apriori knowledge regarding abnormal heart conditions.

These and other features will become apparent by review of the figures and detail descriptions that follow.

BRIEF DESCRIPTION OF THE DRAWINGS

The present invention is described herein with reference to the following drawings. The drawings are provided for purposes of illustration only and not limitation. It should be noted that for clarity and ease of illustration these drawings are not made to scale.

DETAILED DESCRIPTION OF THE PREFERRED EMBODIMENT

Certain embodiments of the invention are described below in connection with the drawings. It should be understood that the invention is not limited by the detailed description and the drawings, but is to be defined by the scope of the appended claims.

Figure 1:
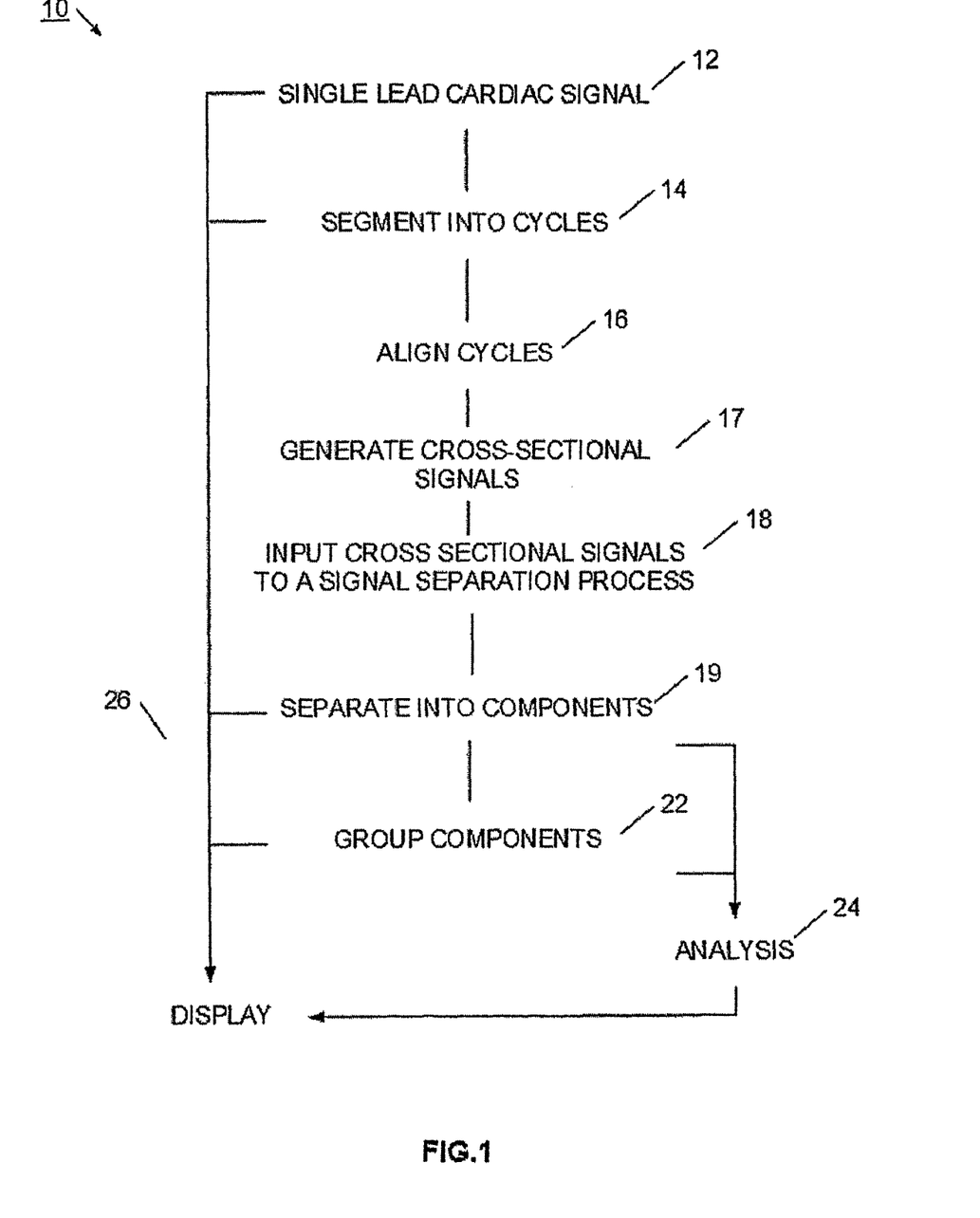
FIG. 1 is a flowchart of a process for decomposing a cardiac signal in accordance with the present invention.

Referring to FIG. 1, a process 10 for decomposing a one-channel ECG signal is illustrated. A single-lead sensor is placed on a patient, which generates a single lead cardiac signal 12. The sensor may be part of an emergency sensor pack, associated with other medical equipment, or may even be incorporated into a device such as a pacemaker that is carried or attached to the patient. The signal 12 may be received from a patient in real-time, or may be recorded and applied to process 10 at a later time. Further, the signal 12 may be generated at one location and transmitted to another location for further processing. For example, the sensor may be attached to the patient, and a wireless radio, or other information-transmitting device, may be used to transmit the cardiac signal to a remote location for further processing and monitoring. The process 10 may be applied advantageously to humans as well as animals. Although significant in certain aspects of the single-lead system, the signal generating step may be independent of the remaining aspects of the process 10.

The process 10 receives the one-channel ECG signal 12, which is typically recorded over a continuous time period.

Figure 6A:
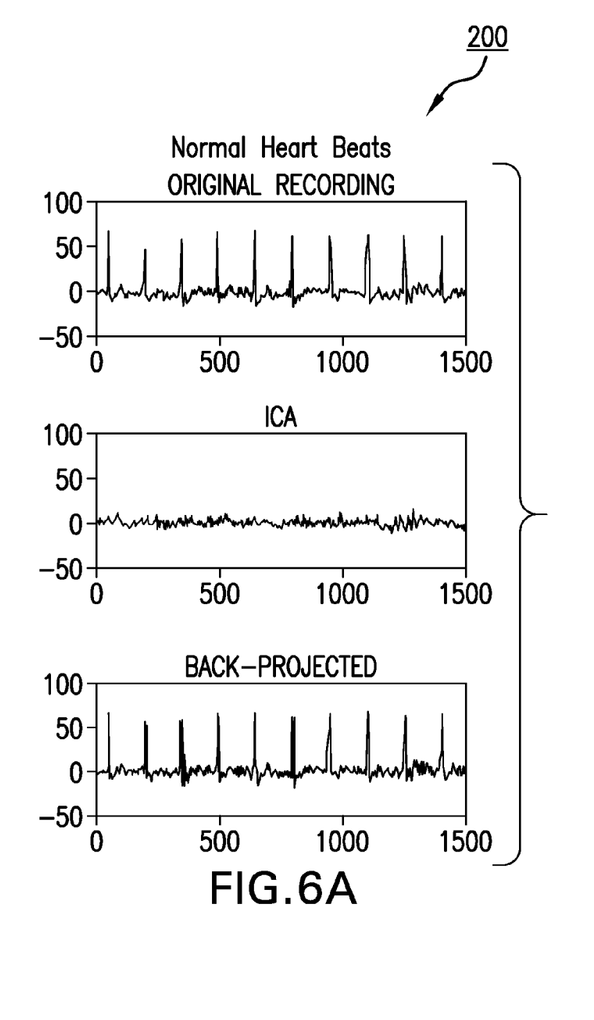
FIG. 6 is an illustration of waveforms derived using a decomposing process in accordance with the present invention.
Figure 6B:
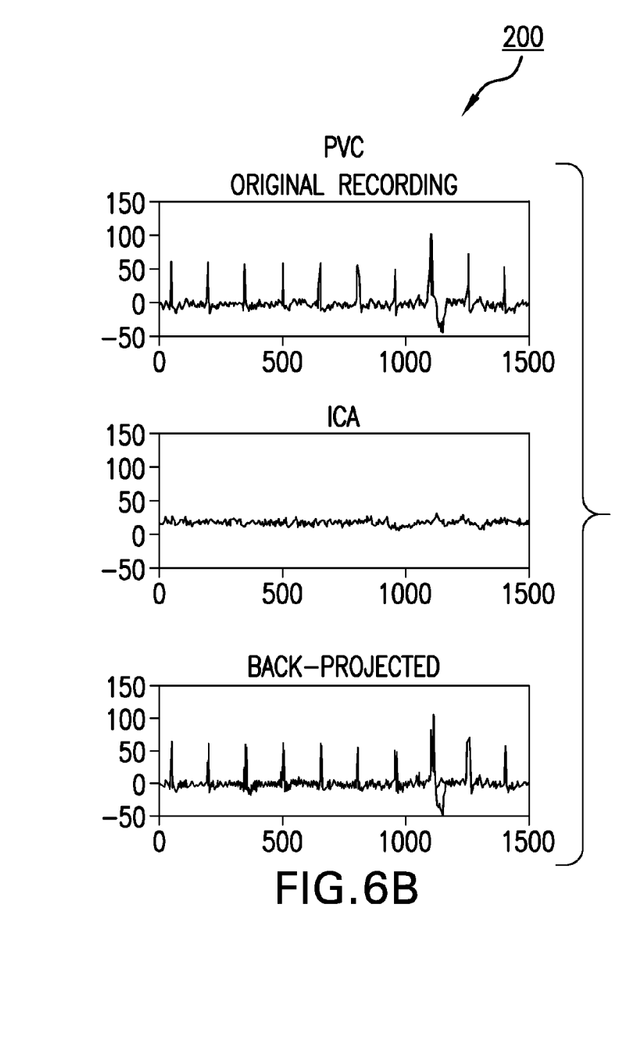

The top left chart and top right chart of FIG. 6 respectively illustrate the recorded one-lead ECG signals of a normal subject and a patient with premature ventricular contraction (PVC). As shown in FIG. 6, ECG signals typically have substantially regular cycles representing heartbeat cycles and corresponding QRS complex wave cycles. The QRS waveform is well known, and will not be discussed in detail. It will be understood that animal species may have other characteristic heart waveforms that may be substituted in the process 10.

Referring back to FIG. 1, the process 10 proceeds to block 14, where the ECG signal is segmented into a set of cycle segments. The detection process of block 14 may use apriori knowledge to assist detecting and aligning heartbeats. This apriori knowledge may be general to a population, or more specific to an individual. In one arrangement, a continuous one-lead ECG signal of 5000 heartbeats is segmented into 5000 cycle segments, each segment consisting of one heartbeat waveform. Although the cycle segments are substantially regular (for example each cycle corresponds to a single QRS complex wave cycle), the signals over the cycles may include slight variations, which may indicate abnormal medical conditions. Different segmentation arrangements are also envisioned, for example, a continuous one-lead ECG signal for 5000 heartbeats may be segmented into 1000 cycle segments, with each cycle segment consisting of 5 heartbeat waveforms. Alternatively, the segments may be from different cycles over a period of time, e.g., two cycles from different dates. Such data can be valuable to determine the progression of different conditions. For example, a patient may have an ECG history which spans several days, months, or years. These historical ECG signals may be segmented and aligned, which may provide insight into disease progression or recovery. An example of one process for detecting heart waveforms and segmenting the ECG signal into cycle segments is described in connection with FIG. 4. It will be understood that more or fewer heartbeats may be used, and that the number of heartbeats in each cycle segment may be selected according to application specific needs. For example, the detection of some heart abnormalities may be enhanced with longer cycle segments (e.g., left/right bundle branch block, etc.), while others may benefit from short cycle segments (e.g., atrial fibrillation, premature ventricular contraction, etc.). It will also be understood that the number of total heartbeats and the length of the cycle segment may be adjustable automatically or under direction of an operator.

Still referring to FIG. 1, the process 10 proceeds to block 16, where the cycle segments are aligned. Typically, the cycle segments will be aligned, for example, according to the peak of QRS complexes or waveform peak latencies. Once aligned, the cycle segments may be assigned a common starting time or other common reference, such as physical or biological marker. With respect to time, each cycle segment may start at a time point "0", and continue to the end of the cycle. For example, if each cycle consists of one heart waveform, then each cycle would start at 0 sec, and continue to about 1.5 seconds, which would accommodate a heart rate as low as 40 beats per minute. Alternatively, it is within the purviews of the process 10 that if each cycle consists of five heart waveforms, then each cycle would start at 0 seconds, and may continue to 6 seconds. It will also be understood that other time frames and references may be used, including physical or biological markers, e.g., P-/Q-/R-/S-/T-wave, pacemaker signal, etc. Of specific interest is aligning the segments, e.g., a QRS complex, based on the R-wave which is generally more easily identifiable. Prior knowledge of potential reference signals may also be used facilitate alignment. This prior knowledge may be specific to a particular patient, or relate of a more general population.

After the cycle segments are aligned according to a common reference, then in block 17 the process 10 generates a set of cross-sectional signals, which may be in the form of time-slice signals. Each time slice signal represents a cross-section of the aligned cycle segments. This process of extracting cross-sectional signals may also be referred to as transposing the aligned waveform dataset. For example, if 5000 heart waveform cycles are aligned, each cross-sectional signal would consist of 5000 data points, with each point representing the same relative time on each waveform cycle. In one example, a time-slice signal is generated for every 0.1 second of the heart waveform cycle. In this example, if each heart waveform is 1.5 seconds in duration, then a time-slice signal would be generated for each of the following 16 time points: 0, 0.1, 0.2, 0.3, 0.4, 0.5, 0.6, 0.7, 0.8, 0.9, 1.0, 1.1, 1.2, 1.3, 1.4, and 1.5. It will be understood that fewer or more time-slice signals may be generated. Also, it will be understood that the sampling frequency does not have to be periodic, that is, the time-slice sampling may be adjusted to obtain a higher resolution at certain time-portions, and lower resolution at others. It will also be appreciated that the sampling may be set according to a reference other than time. For example, the cross-sections may be taken according to peaks or other characteristics of the heart waveform. As referred herein, the term "time-slice" refers to the cross sections based on time or space reference characteristics or other characteristics of the heartbeat.

The set of cross-sectional signals are then aligned and used as signal inputs into a signal separation process as shown in block 18. A signal separation process typically requires several channels of input. In process 10, the multiple channels are provided by the time-slice signals, which have been generated from the single ECG cardiac signal. In block 19, the signal separation process separates the cross-sectional signals into independent components, with each component representing a signal source. For example, the heart may be the source for several signals, representing normal heart functions as well as abnormal activities. It will be understood that some of the resulting components may represent noise sources, or error sources resulting from misalignments or other process errors. These components may be ignored or discarded, or may be used by the system or operator to tune the system, for example, by better placing the single-lead sensor relative to the reference or grounding channel of the signal acquisition system. It will also be understood that some of the components may represent other signal sources, such as leg or arm movements. These too, may be ignored, discarded, or used to tune the system.

In one example, signal separation process(es) 19 includes signal separation techniques known to those skilled in the art, including non-orthogonal transformation methods. Each time slice signal or cross section signal of the aligned cycle segments is considered a channel of input signals to the transformation. The signal separation method is applied to the channels of input signals to separate the cycle segments into statistically substantially-independent components. In one specific implementation, a blind source separation (BSS) or an independent component analysis (ICA) method is used as the signal separation process. Although process 50 may use an ICA process, it will be understood that other signal separation processes may be used in accordance with this disclosure. Many different algorithms for solving the separation can be found in the literature, including some of the better known algorithms such as JADE (Cardos & Souloumiac (1993) IEE proceedings-F, 140(6); SOBI (Belouchrani et al. (1997) IEEE transactions on signal processing 45(2)); BLISS (Clarke, I. J. (1998) EUSIPCO 1998)); Fast ICA (Hyvarinen & Oja (1997) Neural Compuation 9:1483-92); and the like. For a general summary of BSS or ICA techniques applicable in the present invention, see Baxter et al., WO 03/073612; Haykin, Simon. Unsupervised Adaptive Filtering, Volume 1: Blind Source Separation. Wiley-Interscience; (Mar. 31, 2000); Haykin, Simon. Unsupervised Adaptive Filtering Volume 2: Blind Deconvolution. Wiley-Interscience (February 2000); Hyvarinen et al., Independent Component Analysis Wiley-Interscience; 1 edition (May 18, 2001).

Other non-orthogonal transformation methods, such as Varimax, Promax, variational methods and so forth, can also be used. In one experiment, one-lead ECG signals are isolated and time-aligned into 5000 heartbeat cycles, and separated by an ICA method into 150 components. Although process 10 may use an ICA process, it will be understood that other signal separation processes may be used in accordance with this disclosure.

Some abnormal heart signals may be detected or derived directly from the independent components. For example, selected components may be displayed 26 to an operator, who may identify a pattern or signal that indicates a cardiac abnormality. In another example, the independent components are analyzed 24 with an automated process to detect patterns, frequencies, or characteristic signals. Once detected, the process may display 26 the result, present an alarm, or take a predefined action. Although the components may be used for some abnormalities, other abnormalities may benefit from a further processing by optional block 22.

From the block 19, the process 10 optionally proceeds to block 22, where the separated components are organized into component groups. In one example, the components are organized by frequency ranges. For example, since atrial fibrillation is typically represented by cardiac signals between 5 hertz and 8 hertz, components with spectral peaks at the 5-8 hertz range are combined into one component group. The frequencies of components can be determined by conventional methods such as a Fourier transfer. Components can be combined using conventional methods such as adding the component signals together. In one embodiment, the components of certain pre-determined frequency ranges are considered not important for medical purposes, and thus discarded without forming component groups.

It is also possible that a component becomes a component group without combining with other components. For example, if only one of the separated components is within the 5-8 Hertz range, then this component becomes the component group for a possible atrial fibrillation condition. In another example, none of the components is combined with other components, and the block 22 is thus omitted. The process 10 then displays 26 some of the separated components instead of component groups.

Block 26 may be used to display various waveforms used in the process 10, including the single lead cardiac signal, selected segments, selected components, and some or all of the component groups. The component groups may be displayed electronically on a screen or on paper, and reviewed by a physician or other medical personnel. The component groups may be also be used by a monitoring device to monitor a patient's cardiac conditions, and to automatically send warnings or activate a prevention therapy (for example sending electrical stimuli to the patient's heart) based on detected abnormal conditions within the component groups.

Figure 2:
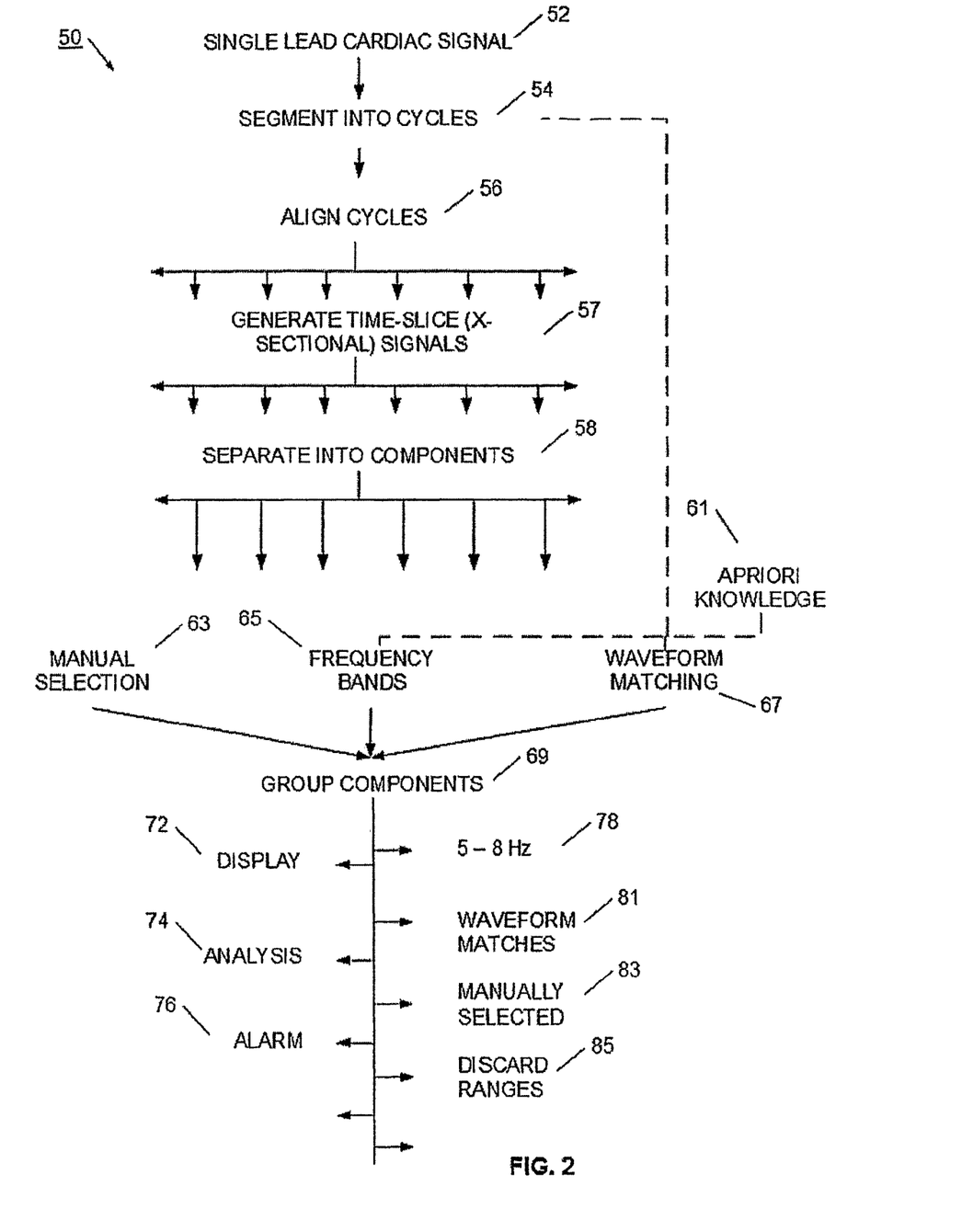
FIG. 2 is a flowchart of a process for decomposing a cardiac signal in accordance with the present invention.

Referring to FIG. 2, a process 50 for decomposing a one-channel ECG signal is illustrated. A single-lead sensor is placed on a patient, and generates a single lead cardiac signal 52. The sensor may be part of an emergency sensor pack, associated with other medical equipment, or may even be incorporated into a device, such as a pacemaker, that is carried or attached to the patient. The signal 52 may be received from a patient in real-time, or may be recorded and applied to process 50 at a later time. Further, the signal 52 may be generated at one location, and transmitted to another location for further processing. For example, the sensor may be attached to the patient, and a wireless radio, or other information-transmitting device, may be used to transmit the cardiac signal to a remote location for further processing and monitoring. The process 50 may be applied advantageously to humans, as well as animals. Although significant in certain aspects of the single lead system, the signal generating step may be independent of the remaining aspects of the process 50.

The process 50 receives the one-channel ECG signal 52, which is typically recorded over a continuous time period. The top left chart and top right chart of FIG. 6 respectively illustrate the recorded one-lead ECG signals of a normal subject and a patient with premature ventricular contraction (PVC). As shown in FIG. 6, ECG signals typically have substantially regular cycles representing heartbeat cycles and corresponding QRS complex wave cycles. The QRS waveform is well known, and will not be discussed in detail. It will be understood that animal species may have other characteristic heart waveforms that may be substituted in the process 50.

Referring back to FIG. 2, the process 50 proceeds to block 54, where the ECG signal is segmented into a set of cycle segments. The detection process of block 54 may use apriori information to assist detecting and aligning heartbeats, which may be from a general population or specific to an individual. In one arrangement, a continuous one-lead ECG signal of 5000 heartbeats is segmented into 5000 cycle segments, each segment consisting of one heartbeat waveform. Although the cycle segments are substantially regular (for example each cycle corresponds to a single QRS complex wave cycle), the signals over the cycles may include slight variations, which may indicate abnormal medical conditions. Similarly, a continuous one-lead ECG signal for 5000 heartbeats segmented into 1000 cycle segments, each cycle segment will consist of 5 heartbeat waveforms. Alternatively, the segments may be from different cycles over a period of time. The detection process of block 54 may use apriori knowledge to assist detecting and aligning heart waveforms. This apriori knowledge may be general to a population, or more specific to an individual. For example, if a patient has a pacemaker, then the generally expected pacemaker signal may be used to assist in detecting and aligning heartbeats. In another example, the EKG of a patient may have been previously taken, and that patient's QRS profile may be used to assist in more accurately detecting and aligning the cycle segments.

An example of one process for detecting heart waveforms and segmenting the ECG signal into cycle segments is described in connection with FIG. 4. It will be understood that more or fewer heartbeats may be used, and that the number of waveforms in each cycle segment may be selected according to application specific needs. For example, the detection of some heart abnormalities may be enhanced with longer cycle segments (e.g., left/right bundle branch block, etc.), while others may benefit from short cycle segments (e.g., atrial fibrillation, premature ventricular contraction, etc.). It will also be understood that the number of total heartbeats and the length of the cycle segment may be adjustable automatically or under direction of an operator.

Still referring to FIG. 2, the process 50 proceeds to block 56, where the cycle segments are aligned. Typically, the cycle segments may be aligned according to waveform peak latencies. For example, the common QRS profile may be used. The QRS complex is the most important and generally recognized feature of a heartbeat signal, of which the R-wave is the most easily identifiable. With the largest amplitude and fastest bouncing (maximum frequency response), it can be easily detected with a simple threshold or slope (first order derivative) technique in most cases. After the QRS waveform is found as a complex or as the independent waveforms (Q-, R-, or S-wave), it is also useful to assist in identifying the P-wave, (typically hundreds of milliseconds before the QRS complex), and T-wave, (typically hundreds milliseconds after the QRS complex). As a result, these waveforms (QRS complex, P-/Q-/R-/S-/T-wave) can be used to align the segmented heartbeat ECG signals prior to generating the cross-sectional signals. Other identifying references may also be used, for example, pacemaker signals if present or other physical or biological marker. Once aligned, the cycle segments may be assigned a common starting time or other common reference. In this way, each cycle segment would start at time point "0", and continue to the end of the cycle. For example, if each cycle consists of one heart waveform, then each cycle would start at 0 sec, and continue to about 1.5 seconds, which would accommodate a heart rate as low as 40 beats per minute. In another example, it each cycle consists of five heart waveforms, then each cycle would start at 0 seconds, and may continue to 6 seconds. It will be understood that other time frames and references may be used. Prior knowledge may be utilized to assist in the alignment of the heartbeats or the cycle segments.

After the cycle segments are aligned according to a common reference, then in block 57 the process 50 generates a set of time-slice signals (the term may or may not be time-dependent as explained herein). Each time slice signal represents a cross-section of the aligned cycle segments. For example, if 5000 heart waveform cycles are aligned, each time-slice signal would consist of 5000 data points, with each point representing the same relative time on each waveform cycle. In one example, a time-slice signal is generated for every 0.1 second of the heart waveform cycle. In this example, if each heart waveform is 1.5 seconds in duration, then a time-slice signal would be generated for each of the following 16 time points: 0, 0.1, 0.2, 0.3, 0.4, 0.5, 0.6, 0.7, 0.8, 0.9, 1.0, 1.1, 1.2, 1.3, 1.4, and 1.5. It will be understood that fewer or more time-slice signals may be generated. Also, it will be understood that the sampling frequency does not have to be periodic, that is, the time-slice sampling may be adjusted to obtain a higher resolution at certain time-portions, and lower resolution at others. It will also be appreciated that the sampling may be set according to a reference other than time. For example, the cross-sections may be taken according to peaks or other characteristics of the heart waveform.

The set of time-slice signals are then aligned and used as signal inputs into a signal separation process as shown in block 58. A signal separation process typically requires several channels of input. In process 50, the multiple channels are provided by time-slice signals, which have been generated from the single ECG cardiac signal. In order to act as parallel inputs to the signal separation process, the time-slice signals are aligned, for example, according to waveform peak values. In block 58, the signal separation process separates the time-slice signals into independent components, with each component representing a signal source. For example, the heart may be the source for several signals, representing normal heart functions as well as abnormal activities. It will be understood that some of the resulting components may represent noise sources, or will be error sources resulting from misalignments or other process errors. These components may be ignored or discarded, or may be used by the system or operator to tune the system, for example, by moving the single-lead sensor. It will also be understood that some of the components may represent other signal sources, such as leg or arm movements. These too, may be ignored, discarded, or used to tune the system.

In one example, separation signal process(es) 58 contemplated by the present invention includes signal separation techniques known to those skilled in the art, including non-orthogonal transformation methods, that separates the cycle segments into statistically substantially independent components. Each time slice signal or cross section signal of the aligned cycle segments is considered a channel of input signals to the transformation. The non-orthogonal method is applied to the channels of input signals to produce independent components. In one specific implementation, a blind source separation (BSS) or an independent component analysis (ICA) method is used as the signal separation process. Although process 50 may use a BSS or an ICA process, it will be understood that other signal separation processes may be used in accordance with this disclosure. For a general summary of BSS or ICA techniques applicable in the present invention, see Haykin, Simon. Unsupervised Adaptive Filtering, Volume 1: Blind Source Separation. Wiley-Interscience; (Mar. 31, 2000); Haykin, Simon. Unsupervised Adaptive Filtering Volume 2: Blind Deconvolution. Wiley-Interscience (February 2000); Hyvarinen et al., Independent Component Analysis Wiley-Interscience; 1 edition (May 18, 2001);

Some abnormal heart signals may be detected or derived directly from the independent components. For example, selected components may be displayed 72 to an operator, who may identify a pattern or signal that indicates a cardiac abnormality. In another example, the independent components are analyzed 74 with an automated process to detect patterns, frequencies, or characteristic signals. Once detected, the process may display 72 the result, present an alarm 76, or take a predefined action.

Process 50 may include apriori knowledge 61 regarding cardiac signals. This apriori knowledge may include information regarding normal or abnormal signal information, and may be useful to various aspects of the process 50. For example, the apriori knowledge may be useful for analyzing separated components, for identifying more efficacious placement of the probe(s), for arranging components into component groups, for determining the logical parameters of separation, or for assisting in detecting a real-time abnormal condition. The apriori knowledge may include information such a frequency ranges 65 known to correspond to heart signals or reference waveforms 67 that may indicate normal or abnormal conditions. The apriori knowledge may be pre-loaded, or may be adjusted through an adaptive process. It will also be understood that the apriori knowledge may be general knowledge applicable to a wide group, but may also include information tuned for a single individual. In this way, the process 50 is adapted to a particular individual.

From the block 58, the process 50 proceeds to block 69, where the separated components are organized into component groups. Component groups may be manually selected 63 by medical personnel. Alternatively, the components may be selected with reference to the apriori knowledge 61, such as frequency 65 or reference waveforms 67. For example, since atrial fibrillation is typically represented by cardiac signals between 5 hertz and 8 hertz, components with spectral peaks within the 5-8 Hertz range are combined into one component group 78. The frequencies of components can be determined by conventional methods such as a Fourier transfer. Components can be combined using conventional methods such as adding the component signals together. In one embodiment, the components of certain pre-determined frequency ranges are considered not important for medical purposes, and thus discarded 85. A component that matches a stored signal pattern is added to a component group 81 representing the reference waveform 67. Optionally, multiple components that match the same stored signal pattern can be combined into one component group. The reference waveforms 117 also preferably stores a name for each of the signal patterns, so that a component group can be displayed along with the stored name to better explain the information to the reader.

Block 72 may be used to display various waveforms used in the process 50, including the single lead cardiac signal, selected segments, selected components, and some or all of the component groups. The component groups may be displayed electronically on a screen or on paper, and reviewed by a physician or other medical personnel. The component groups may be also be used by a monitoring device to monitor a patient's cardiac conditions, and to automatically send warnings or activate a prevention therapy (for example sending electrical stimuli to the patient's heart) based on detected abnormal conditions within the component groups.

The process 50 may also include analysis processes 74 or routines that automatically detect abnormal cardiac signals, or provide precursor information that assists a human in identifying the abnormality. The process 50 may also include an alarm 76 that acts responsive to detecting an abnormal cardiac signal. For example, the alarm may be a display, a light, a buzzer or other audible device. Further, the alarm may be an automated medical response, such as a pace-maker circuit for stimulating the heart, or may activate an external device to administer electrical or chemical treatment.

The process 50 may be used to identify numerous cardiac abnormalities. For example, an atrial fibrillation (AF) may be identified by a 5-8 Hz oscillatory signal, which may be indicative of abnormal continuous atrial contraction. In another example, a premature ventricular contraction (PVC) may be identified by isolating a temporal pattern with slow recovery waveform after R peak. As shown in FIG. 6, this PVC indicator is very clearly defined and can be used to select component related to the PVC heartbeats. In another example, a left/right bundle branch block (LBBB/RBBB) may be indicated by a lack of QRS complex waveform in some of the segment cycles. The frequency of this missing waveform indicates the severity of this cardiac disease. With single channel ECG signal decomposition covering several heartbeats on the way (with or without overlaps), the feature can be revealed and the frequency of absence can be figured out at the same time. Those of skill in the art will readily recognize patterns indicative of abnormal cardiovascular conditions.

Figure 3:
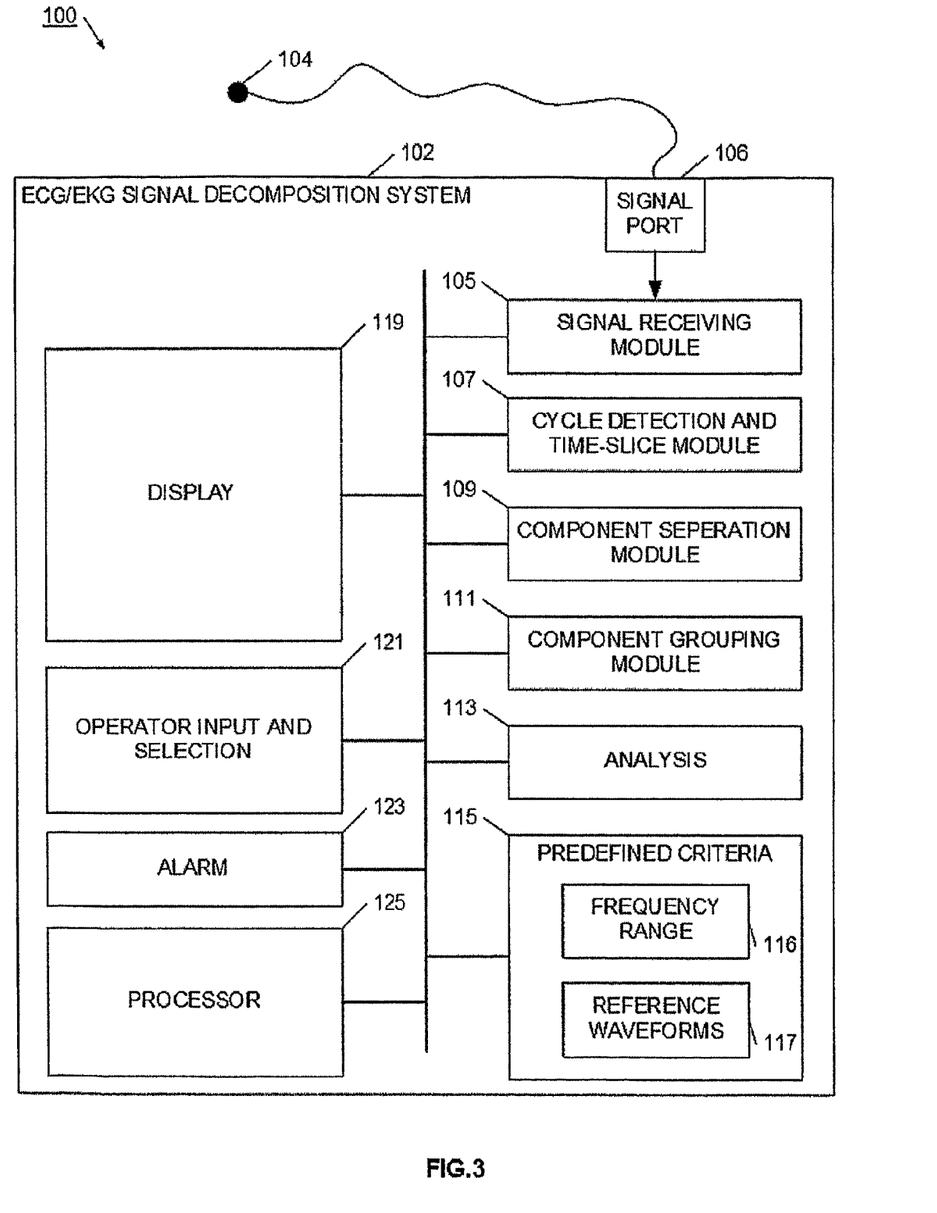
FIG. 3 is a block diagram of a device for decomposing a cardiac signal in accordance with the present invention.

FIG. 3 illustrates one example of a device 100 for decomposing one-channel ECG signals. In specific arrangements, the device 100 of FIG. 3 may be useful to operate the process discussed with reference to FIG. 1 or FIG. 2. The ECG signal decomposition device 100 includes a housing 102. Depending on the specific application, the housing may be constructed as a table-top medical instrument, a portable suitcase, a handheld device, or even a case for implanting in-vivo. It will be understood that the accessories included within the housing 102 may be adjusted according to the specific application. For example, an in vivo housing may not require a display, but is likely to require a battery power source. In another example, a table-top medical instrument may have a power supply, full keyboard, large display, and a printer. It will also be understood that some items and modules may be either inside or outside the housing 102. For example, a handheld housing may have a limited integral display, and provide a port for connecting a full-size display. The reorganization of components and modules may be done according to application specific needs and the desires of the attending medical personnel.

One example of such devices include generally a cardiac signal detection system and method, which is suitable for use in cardiac therapy and monitoring equipment and other similar devices which incorporate techniques of ECG processing and analysis. These devices may include out-of-hospital or in-hospital, external automatic defibrillator (AED), implantable pulse generators (IGPs, e.g., pacemakers), implantable cardioverter-defibrillators (ICDs), insertable loop recorders (ILRs), and the like, which are adapted for sensing cardiac events and, more particularly, to such devices that provide long term monitoring of an electrocardiogram (ECG or EKG) and/or electrograms (EGMs) of a patient. Such devices will typically have limited number of applied or active sensors which impacts their utility, e.g., only utilizing one signal. Separation of multiple signals from such limited sensors greatly enhances or enables their primary utility. More particularly, the present invention relates to a system and method capable of discriminating ventricular fibrillation (VF), ventricular tachycardia (VT), non-shockable tachyarrhythmia, high-frequency noise, using an ECG complexity measure CM, electronic atrial pacing, atrial flutter, ectopic atrial rhythm, sinus rhythm, junction rhythm and atrial fibrillation, including asystole, tachycardia, trigeminy, bradycardia, bigeminy, electrical alternans—pericardial effusion, and the like.

Appropriate handling of noise and non-physiologic signal artifacts have always been an issue in cardiac devices and various measures have been applied, though most involve the use of an automatically adjusting sensing threshold. Accordingly, an alternate embodiment of the present invention relates to configurable multi-threshold noise rejection techniques and apparatus for carrying out such techniques. Such techniques of the present invention can be designed to avoid sensing T-waves, P-waves, myopotential, noise and other artifact signals typically present in an ECG or EGM. Even more particularly, the present invention relates to discrimination of noisy physiologic data from relatively noise free physiologic data and selective storage or display thereof in a medical device or a graphic user interface, respectively.

The device 100 has a signal port 106 for receiving a single-lead cardiac signal. The signal port is constructed to connect to a single-lead sensor 104, which generates the single-lead cardiac signal. The sensor may be an electrode located at any desired location within or in proximity to the heart. Preferably, the sensor is coupled to an amplifier or amplifying means and can be one of many sensors placed within or in proximity to the heart. Although device 100 shows a direct connection, it will be appreciated that the sensor 104 may be remote from the housing 102, and that the cardiac signal is communicated wirelessly. Also, it will be understood that the cardiac signal may be recorded, and then communicated into the signal port 106 at a later time. The signal port may include filtering, amplification, or other well-known pre-processing circuitry. The signal port communicates the cardiac signal to the signal receiving module 105, which may further filter, process, or amplify the signal. Also, the signal receiving module may digitize the cardiac signal into a digital data stream. The use and application of analog to digital converters is well known, so will not be discussed in detail.

The cycle detection module 107 segments the cardiac signal into a set of substantially regular cycle segments. For example, the module 107 may be constructed to detect R-waves in the cardiac signal and separate the signals into QRS complex wave cycle segments based on the detected R-waves. It will be understood that other waveform detection processes may be used. The module 107 also aligns the cycle segments, for example, according to detected peaks. In this way, the cycle segments are aligned to act as inputs to a signal separation module 109. The cycle detection module 107 also aligns the cycles according to a common reference, and generates a set of signals indicative of a cross section of the aligned cycles. Additional detail on generating cross-sectional signals was discussed with reference to FIG. 1 and FIG. 2. Referring again to FIG. 3, each of the generated cross-sectional signals (or time-slice signals) becomes one channel input to the separation module 109. For example, if the cardiac signal is a continuous signal of 5000 waveforms, and each cycle segment is 5 waveforms (about 6 seconds), then module 107 aligns 1000 cycle segments and generates a set of time-slice signals. If a periodic sampling of 0.05 seconds is used, then 121 time-slice signals would be generated. The set of 121 time-slice signals is aligned and used as input to the signal separation process.

The component separation module 109 accepts the cycle segments as input signals, and uses a signal separation process to separate the input signals into statistically substantially independent components. In one example, the signal separation process is a non-orthogonal transformation method, such as an independent component analysis (ICA) process.

The device 100 may include a component grouping module 111, which arranges the separated components into component groups. In one example, the module 111 combines components within a pre-determined frequency range into a single component group, based on frequency ranges stored in the frequency ranges storage module 116. The frequency range storage module 116 preferably stores those frequency ranges that are pre-determined to correlate to particular categories, such as normal QRS complex, atrial fibrillation, premature ventricular contraction, and so forth. In a preferred embodiment, the storage 116 also stores the names of frequency ranges, so that the names can be later displayed by the display module 119. For example, for the stored frequency range of 5-8 Hertz, the name can be "atrial fibrillation" or "5-8 Hz". The display module 119 then displays the component groups. The frequency ranges storage module 116 can also store frequency ranges of unwanted signals, so that the separated components that are within these frequency ranges are discarded and not displayed.

The device 100 may also include other predefined criteria 115, including pre-determined reference waveforms 117 or signal patterns of typical cardiac signals, such as a normal QRS complex wave, a typical signal wave that represents atrial fibrillation, a typical signal wave that represents premature ventricular contraction, and so forth. The component group module 111 may then use the reference waveforms 117 to match components with the stored signal patterns. A component that matches a stored signal pattern is added to a component group representing the reference waveform. Optionally, multiple components that match the same stored signal pattern can be combined into one component group. The reference waveforms 117 also preferably stores a name for each of the signal patterns, so that a component group can be displayed along with the stored name to better explain the information to the reader.

Although the grouping process may be automated, in some cases it may be desirable to have an operator make grouping decisions. In this way, a human operator conducts an initialization session to determine which of the separated components are to be displayed or organized into component groups. For example, a physician or technician may review the separated components to determine which of the separated components should each be displayed or added to a component group, and which of the components do not contain significant medical information and should not be displayed or used. The device stores the human determination of component group organization, and automatically displays or uses the selected channels in later sessions.

The device 100 may also include analysis modules 113 or routines that automatically detect abnormal cardiac signals, or provide precursor information that assists a human in identifying the abnormality. The inclusion of an analytical module 113 will depend on application specific needs. For example, an in-vivo device will need an automated process or module to detect an abnormal condition, while a desktop or handheld device may rely more fully on human identification. The device 100 may also include an alarm 123 that acts responsive to detecting an abnormal cardiac signal. For example, the alarm may be a display, a light, a buzzer or other audible device. Further, the alarm may be an automated medical response, such as a pace-maker circuit for stimulating the heart, or may activate an external device to administer electrical or chemical treatment. Depending on the use and the housing configuration, the device 100 may have operator input 121 keys or controls.

The word "module" refers to one or more physical devices or computer instructions in hardware or software form that carry out certain functions. Modules can be combined or separated into fewer or more modules. Modules need not be located at the same physical location. For example, a module that records or receives ECG signals can be connected using a wired or wireless network to a remotely located module that isolates and separates the signals. The modules may be separate circuitry, or may be operated as processes on a shared resource, such as processor 125.

Processor 125 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor executes instructions stored in digital memory to provide functionality as described below. Instructions provided to processor may be executed in any manner, using any data structures, architecture, programming language and/or other techniques. Digital memory is any storage medium capable of maintaining digital data and instructions provided to processor such as a static or dynamic random access memory (RAM), or any other electronic, magnetic, optical or other storage medium.

In one embodiment, the modules of FIG. 3 can be integrated into one device. For example, an ECG device includes a 1-lead sensor to record ECG signals from a patient, a data storage unit to store the recorded ECG signals over a continuous time period, one or more processing units that process the stored signals to isolate into cycles and to separate into components, and optionally organize the components into component groups, and a display unit that displays the separated components or the organized component groups. A physician or nurse can thus observe the components or component groups as ECG signals are recorded. The modules may include computer instructions in software or hardware form, and can be implemented in one or more microprocessor chips.

In another example, the device can be an implantable medical device (IMD) connected to monitor a patient's heart. IMD may be further configured to integrate both monitoring and therapy features, as will be described herein. IMD suitably collects and processes data about heart from one or more sources (e.g. heart rate monitor, blood pressure monitor, electrocardiogram (ECG) waveform, electrogram (EGM) waveform, or more generally PQRST waveform, or portion of such waveform, etc.). IMD may further provide therapy or other response to the patient as appropriate, and as described more fully below. IMD may be generally flat and thin to permit subcutaneous implantation within a human body, e.g., within upper thoracic regions or the lower abdominal region. IMD may include a hermetically-sealed housing that encloses a processor, a digital memory, and other components as appropriate to produce the desired functionalities of the device. In various embodiments, IMD is implemented as any implanted medical device capable of measuring the heart signal of a patient, including, but not limited to a pacemaker, defibrillator, electrocardiogram monitor, blood pressure monitor, drug pump, insulin monitor, or neurostimulator. Alternately, it can be an external medical device configured to integrate both monitoring and therapy feature such as an AED.

The system and processes of FIGS. 1-3 use a signal separation process to generate a set of source signal components. Although a non-orthogonal transformation, specifically an ICA or BSS, has been discussed, it will be appreciated that other signal separation processes may be used. Generally, signal separation techniques are aimed to recover N source signals, $s=\{s1(t), \ldots, sN(t)\}$, (e.g., different voice, music, or noise sources) after they are mixed by multiplying by A, an unknown matrix, $x=\{x1(t), \ldots, xN(t)\}=As$, while assuming as little as possible about the natures of A or the component signals. The mixing matrix, A, could be linear, non-linear, time-invariant or time-variant. Specifically, one tries to recover a version, $u=Wx$, of the original sources, s, identical save for scaling and permutation, by finding a matrix, W, specifying filters that invert the mixing process. An example of signal separation technique for linear mixing is Principal Component Analysis (PCA). The basic idea in PCA is to find the components, $s=\{s1(t), \ldots, sN(t)\}$, so that they explain the maximum amount of variance possible by N linearly transformed components. To this end, PCA uses second-order statistics (the data covariance matrix) to decorrelate the sources. Because each component of PCA is defined to maximize the variability that is not captured by other components, components are uncorrelated or orthogonal to each other. Variance maximizing (Varimax) is often used in conjunction with PCA to rotate components s derived by PCA toward a "simpler structure. PCA, with or without Varimax, is most effective if underlying sources have Gaussian distributions. However, because it produces an orthogonal rotation, Varimax components derived from PCA eigenvectors cannot account for sources whose projections to the sensors are non-orthogonal or whose statistical distributions are non-Gaussian.

Another approach for signal separation involves a non-orthogonal or oblique rotation method such as Independent Component Analysis (ICA) or Blind Source Separation (BSS). ICA and blind source separation can be found in, for example, A. J. Bell and T J Sejnowski, Neural Computation 7:1129-1159 (1995)); Te-Won Lee, Independent Component Analysis: Theory and Applications, Kluwer Academic Publishers, Boston, September 1998, Hyvarinen et al., Independent Component Analysis, 1st edition (Wiley-Interscience, May 18, 2001); Mark Girolami, Self-Organizing Neural Networks: Independent Component Analysis and Blind Source Separation (Perspectives in Neural Computing) (Springer Verlag, September 1999); and Mark Girolami (Editor), Advances in Independent Component Analysis (Perspectives in Neural Computing) (Springer Verlag August 2000). Single value decomposition algorithms have been disclosed in Adaptive Filter Theory by Simon Haykin (Third Edition, Prentice-Hall (NJ), (1996).

ICA uses statistics of all orders and pursues a more ambitious objective. While PCA simply decorrelates the outputs (using an orthogonal unmixing matrix W), ICA attempts to make the outputs statistically independent, while placing no orthogonal constraints on the unmixing matrix W. It is thus more feasible for biomedical source separation.

Figure 4:
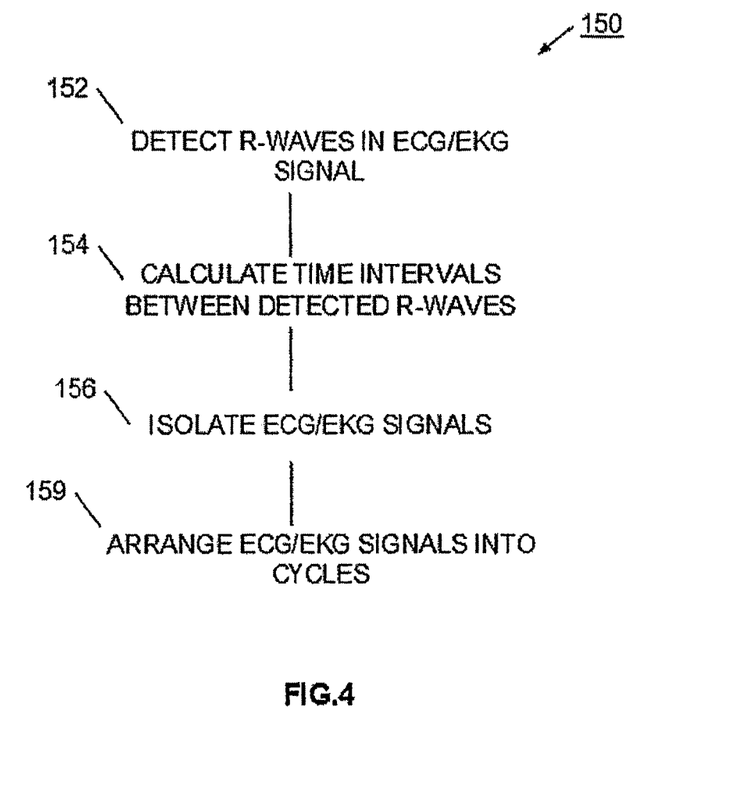
FIG. 4 is a flowchart of a process for detecting heart waveforms in accordance with the present invention.

FIG. 4 illustrates one embodiment of a process 150 of isolating a channel of recorded ECG signals into cycle segments. A cycle segment is a portion of the recorded ECG signals over a continuous time period that approximately repeats itself over the same time period. Signals of different cycles may have small variations in frequency, amplitude and duration. The process 150 proceeds to a block 152 to detect characteristics that indicate cycles in the recorded ECG signals. Since QRS complex waves are typically dominant in recorded ECG signals and typically repeat in substantially regular cycles, the recorded ECG signals are preferably isolated into QRS complex cycles. Since R-waves typically represent the highest points in QRS complex cycles, R-wave detection is a preferred way of identifying QRS complex cycles.

R-waves can be detected by various methods, for example by calculating the correlation between recorded ECG signals and a triangle template. The triangle template can be represented by a matrix d such as d=[0 0 0 1 3 5 3 1 0 0 0] with N time points. N represents the number of time units in the triangle template, for example the number of seconds in the triangle template. The following formula $$r = \frac{\sum_i (x_i - \bar{x})(d_i - \bar{d})}{N \sqrt{\frac{\sum_i (d_i - \bar{d})^2}{N}} \sqrt{\frac{\sum_i (x_i - \bar{x})^2}{N}}}$$

is used to calculate the correlation between the recorded ECG signals and the triangle template. In the equation above, xi represents the recorded ECG signal at time point i, r represents the correlation coefficient between the recorded ECG signals and the triangle template. For the recorded ECG signals over M continuous time points, correlation coefficients rj are calculated with j=1, . . . , M. With the correlation coefficients plotted over the M continuous time points, the coefficients achieve peak values at time points near the occurrence of R-waves. The correlation coefficients over the M time points, which correspond to the recorded ECG signals over the M time points, are then searched to detect R-waves.

A minimum correlation coefficient threshold value can be used to limit the search area over the M time points. In one embodiment, with correlation coefficient values in the range between 0 and 1, only the subsections where the correlation coefficients are greater than a minimum threshold of 0.6 are searched for R-wave detection. The insignificant subsections with coefficients less than or equal to 0.6 are thus eliminated. The plotted correlation coefficients and corresponding recorded ECG signals over M continuous time points are thus separated into a number of subsections, with each subsection having correlation coefficient values greater than the threshold value. For every subsection of the recorded ECG signals, the local maximum is identified as the R-wave peak point. In another embodiment, which does not require a threshold value, each point above a certain correlation coefficient value, such as 0.8 or 0.9, is identified as an R-wave peak point.

Other methods can also be used to detect R-waves. In one arrangement, after a R-wave is detected, the detected R-wave and a determined heartbeat rate can be used to predict the occurrence of other R-waves. For instance, if the patient's heartbeat rate is determined to be approximately 800 ms per beat, then the areas approximately 800 ms before and after a detected R-wave can be considered likely R-wave occurrences, and only such areas need to be investigated to detect R-waves. For example, the local maximum in the area between 750 ms and 850 ms after a detected R-wave can be identified as the R-wave peak point.

In another arrangement, instead of a simple triangle template, a more complex template, such as a template formed as a linear mixture of multiple triangle waves, can also be used. Instead of detecting R-waves, other waves, for example P-waves, Q-waves, ST segments or the combinations of a Q-wave and a R-wave, can also be detected for the purpose of isolating QRS cycles in recorded ECG signals.

Still referring to FIG. 4, the process 150 proceeds from the block 152 to a block 154, where the process 150 calculates the time intervals between adjacent detected R-waves. In one embodiment, in order to take into account the heart rate variability over time, the process 150 first calculates, for a plurality of pairs of adjacent detected R-waves, the time interval between each of the pairs of R-waves, and then calculates the average or mean of the time intervals. In another embodiment, the process 150 calculates the total time interval T between a first detected R-wave and an n-th detected R-wave, and then calculates the average time interval T/(n−1) as the time interval between adjacent R-waves.

The process 150 then proceeds to a block 156 to isolate the recorded ECG signals into cycles based on the detected R-waves and based on the calculated time intervals. For example, if the time interval between two adjacent detected R-waves is 800 ms, the process 150 isolates a QRS complex cycle as starting at 400 ms before a detected R-wave and ending at 400 ms after the detected R-wave. The process 150 may also isolate a signal cycle as, for example, starting at 600 ms before a detected R-wave and ending at 200 ms after the detected R-wave. Process 150 then arranges the ECG signals into cycle segments as shown in block 159.

For some patients with abnormal medical conditions, such as left bundle branch block and right bundle branch block, the recorded ECG signals may include large variations of QRS complex cycle times. In some heartbeat cycles, it is even possible that an R-wave cannot be detected. For example, for a series of 100 heartbeat cycles of continuously recorded ECG signals, it is possible that only 80 R-waves are detected using the above-described triangle template and correlation coefficient method. Therefore, only the QRS cycles with detected R-waves are isolated as input signals for a non-orthogonal transformation. Even if a detected R-wave is not adjacent to another detected R-wave in the recorded ECG signals, a cycle can be isolated based on the detected R-wave and based on the time interval of a QRS cycle. For example, if the heartbeat cycle (and corresponding QRS cycle) time interval is 800 ms, the process may isolate a cycle as starting at 400 ms before a detected R-wave and ending at 400 ms after a detected R-wave.

Figure 5:
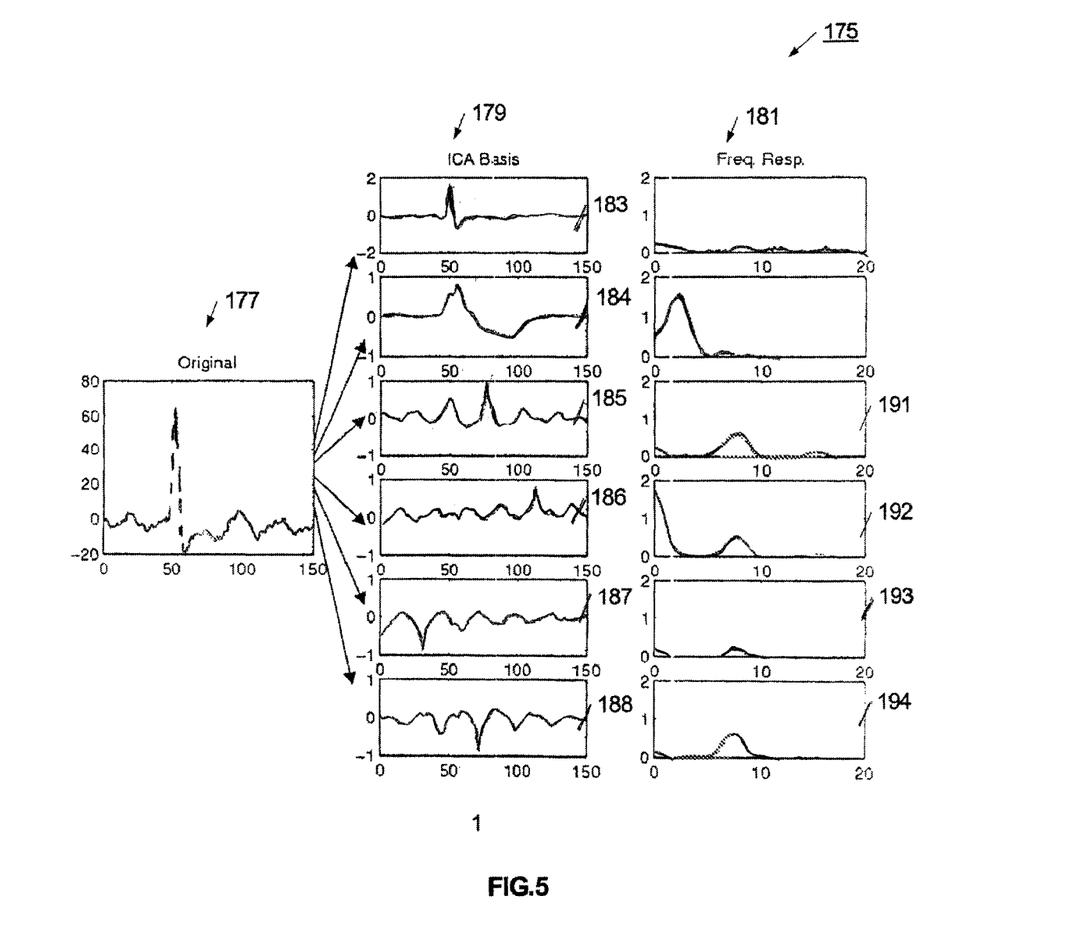
FIG. 5 is an illustration of waveforms derived using a decomposing process in accordance with the present invention.

FIG. 5 illustrates waveform displays 175, which include a cardiac cycle of ECG signals 177, some of the separated components 179, and the frequency representation for each of the displayed components 181. The left column 177 of FIG. 5, under the heading "Original", shows a QRS complex cycle of originally recorded ECG signals. A series of recorded ECG signals are isolated into QRS cycles based on R-wave detection, and separated using an ICA method into components. The middle column 179, under the heading "ICA basis", shows six of the separated components (also called basis), each with its frequency representation shown in a right column 181 chart under the heading "Freq. Resp."

Referring now from top to bottom to the six charts of the middle column, each of the six charts shows a separated component. The first chart 183 (the first component) mainly represents the normal QRS complex of normal heartbeats. The second component 184 mainly represents the abnormal premature ventricular contraction heartbeats. The third to sixth (185-188) components mainly represent arrhythmic flutters. The third to sixth components (185-188) have frequency peaks at the range of 5-8 hertz, as shown in the associated frequency response waveforms 191-194. In a preferred embodiment, the third to sixth components (185-188) are combined into one component group based on their common frequency range of 5-8 hertz.

FIG. 6 illustrates the recorded ECG signals 200 and a separated component group for a normal subject and a patient with premature ventricular contraction (PVC). For the left and right columns under the headings "Normal Heart Beats" and "PVC" respectively, the top chart shows a one-channel original ECG recording. The middle chart shows an ICA-separated and organized component group that indicates a likely atrial fibrillation condition. The bottom chart shows the middle chart signals back projected onto the top chart original signals. The premature ventricular contraction (PVC) may be identified by isolating a temporal pattern with slow recovery waveform after R peak. As shown in FIG. 6, this PVC indicator is very clearly defined and can be used to select component related to the PVC heartbeats.

The disclosed process can be applied to not only 1-lead ECG recordings, but also one or more channels of 12-lead or 3-lead ECG signals. For example, the process can be applied serially or in parallel to each of the 3 channels of 3-lead ECG signals. The process can be applied to one of the 3 or 12 leads that is determined to provide the best results. Our experiments have shown that in a typical 3-lead arrangement, the 2nd lead often provides the best results for detecting atrial fibrillation.

In addition to atrial fibrillation, the disclosed system and process can also be utilized to detect other medical conditions. For example, some of the component groups may display wave patterns to indicate diseases such as Wolff-Parkinson-White (WPW) syndrome, ventricular hypertrophy, and so forth. Component groups may indicate sub-types of abnormal heartbeats such as ventricular tachycardia and so forth. The component groups may be used to detect other conditions such as sinus arrhythmia, wandering atrial pacemaker, multifocal atrial tachycardia, atrial flutter, agonal rhythm, torsades de pointes, first-degree AV block, wenchebach, type II second-degree AV block, and so forth. The component groups can be used to detect ST segment augmentation or Q-wave abnormalities, which may indicate myocardial infarction. In addition to ECG signals, the disclosed system and process can also be used to decompose other one-channel signals, particularly those signals that can be isolated into substantially regular cycles.

In an alternate embodiment, the present invention is directed to an analytic tool for analyzing cardiac signals. A cardiac signal is segmented into a set of cycle segments according to detected heartbeats. The cycle segments are aligned, and a set of signals is generated, with each signal representing a cross section across the aligned cycle segments. The cross-sectional signals are then presented as inputs to a signal separation process, which separates the cardiac signal into a set of components. The components may be grouped according to predefined criteria. The components or groups may be analyzed or displayed to assist in the detection of an abnormal cardiac signal, which may be indicative of an abnormal heart condition. In one example, the signal separation process is a non-orthogonal transformation method such as independent component analysis (ICA).

Although the foregoing has described certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not to be limited by the preferred embodiments, but is to be defined by reference to the following claims.

What is claimed is:

1. A method of analyzing an electrocardiogram (ECG) signal, the method comprising:
   receiving the ECG signal;
   segmenting the received ECG signal into a set of cycle segments;
   aligning the set of cycle segments along a relative time axis to obtain aligned cycle segments;
   generating a set of cross-sectional signals from the aligned cycle segments, wherein each cross-sectional signal is a time-slice signal representing a cross-section of the aligned cycle segments along a relative time of the aligned cycle segments, said each cross-sectional signal corresponding to a different relative time;
   separating, using a signal separation process, the set of cross-sectional signals into a set of statistically substantially independent components; and
   detecting, using the set of components, an abnormal cardiac signal;
   wherein the steps of receiving, segmenting, aligning, generating, separating, and detecting are performed by a processor-based cardiac signal detection system.

2. The method of claim 1, further comprising the steps of
   selecting a plurality of the independent components that match a predefined criteria; and
   arranging the selected independent components into a component group.

3. The method of claim 2, wherein the detecting step comprises detecting the abnormal cardiac signal in the component group.

4. The method of claim 2, wherein the selecting step comprises choosing in accordance with one or more predefined criteria, the one or more predefined criteria comprising one or more frequency criteria, and one of the component groups is arranged to have independent components matching the one or more frequency criteria.

5. The method of claim 2, further comprising displaying at least one of the arranged component groups and a name identifying the predefined criteria.

6. The method of claim 2, further comprising displaying the component group.

7. The method of claim 1, further comprising the steps of:
   displaying at least some of the independent components to an operator;
   receiving from the operator instructions to select a plurality of the independent components; and
   arranging the selected independent components into a component group.

8. The method of claim 1, wherein segmenting the received ECG signal comprises isolating the received ECG signal into a set of QRS complex wave cycle segments.

9. The method of claim 1, wherein aligning the cycle segments comprises detecting an R-wave peak point of each of the cycle segments.

10. The method of claim 1, wherein aligning the cycle segments comprises detecting a P-wave peak point of each of the cycle segments.

11. The method of claim 1, wherein aligning the cycle segments comprises detecting a Q-wave peak point of each of the cycle segments.

12. The method of claim 1, wherein aligning the cycle segments comprises detecting a R-wave peak point of each of the cycle segments and calculating time intervals between adjacent R-wave peak points.

13. The method of claim 1, wherein segmenting the received ECG signal comprises arranging each cycle segment to have one and only one heart waveform cycle.

14. The method of claim 1, wherein segmenting the received ECG signal comprises arranging each cycle segment to have a plurality of heart waveform cycles.

15. The method of claim 1, wherein separating the set of cycle segments comprises using a non-orthogonal transformation.

16. The method of claim 1, wherein separating the set of cycle segments comprises using an independent component analysis process.

17. The method of claim 1, wherein the receiving step comprises receiving the ECG signal as a one channel ECG signal from a single lead sensor.

18. The method of claim 1, wherein the receiving step comprises receiving the ECG signal from one channel from a multi-lead sensor.

* * * * *